United States Patent [19]

Baleiko et al.

[11] Patent Number: 4,599,144

[45] Date of Patent: Jul. 8, 1986

[54] PROCESS FOR RECOVERY OF METHACRYLIC ACID

[75] Inventors: Marc O. Baleiko, Naperville; Edward F. Rader, Wheaton, both of Ill.

[73] Assignee: Standard Oil Company (Indiana), Chicago, Ill.

[21] Appl. No.: 624,049

[22] Filed: Jun. 25, 1984

[51] Int. Cl.$^4$ ................................. B01D 3/36
[52] U.S. Cl. ............................. 203/15; 203/52; 203/68; 203/91; 203/99; 203/DIG. 19; 203/DIG. 21; 562/600; 562/608
[58] Field of Search .............. 203/15, 68, 91, 69, 203/70, 99, DIG. 19, DIG. 21, 14, 52; 562/600, 599, 608

[56] References Cited

U.S. PATENT DOCUMENTS

| | | | |
|---|---|---|---|
| 3,433,831 | 3/1969 | Yomiyama et al. | 203/DIG. 21 |
| 3,840,587 | 10/1974 | Pearson | 562/598 |
| 3,844,903 | 10/1974 | Willersinn et al. | 203/15 |
| 3,926,744 | 12/1975 | Noll et al. | 203/63 |
| 4,039,428 | 8/1977 | Wei | 203/DIG. 19 |
| 4,040,913 | 8/1977 | Clovis et al. | 203/77 |
| 4,085,143 | 4/1978 | Holmes | 562/599 |
| 4,142,058 | 2/1979 | Matsumura et al. | 562/608 |
| 4,147,721 | 4/1979 | Leacock | 203/DIG. 21 |
| 4,166,774 | 9/1979 | Wagner | 562/600 |

FOREIGN PATENT DOCUMENTS

| | | | |
|---|---|---|---|
| 0159832 | 3/1964 | Bulgaria | 562/600 |
| 0721773 | 11/1965 | Canada | 562/599 |
| 0115317 | 9/1979 | Japan | 203/15 |
| 1120284 | 7/1968 | United Kingdom | 562/600 |

*Primary Examiner*—S. Leon Bashore
*Assistant Examiner*—V. Manoharan
*Attorney, Agent, or Firm*—James R. Henes; William T. McClain; William H. Magidson

[57] ABSTRACT

Process is disclosed for treating the reaction product of propionic acid and formaldehyde to recover methacrylic acid from an aqueous effluent wherein said effluent contains methacrylic acid, unreacted formaldehyde, unreacted propionic acid, water and by-products.

14 Claims, No Drawings

PROCESS FOR RECOVERY OF METHACRYLIC ACID

FIELD OF THE INVENTION

In general, the field of this invention relates to a method of distilling the reaction product stream from reaction of a saturated aliphatic monocarboxylic acid compound and formaldehyde, said reaction product stream comprising saturated aliphatic monocarboxylic acid compound, an alpha,beta-ethylenically unsaturated aliphatic monocarboxylic acid compound of one more carbon atom than the starting saturated aliphatic monocarboxylic acid compound, water and formaldehyde wherein unreacted saturated aliphatic monocarboxylic acid compound and unreacted formaldehyde are removed from the product stream and can be recycled back to the reactor.

In more specific terms, the field of this invention relates to a process for recovery of methacrylic acid from an aqueous effluent obtained by the vapor phase aldol-type condensation of propionic acid and formaldehyde wherein the effluent contains methacrylic acid, unreacted propionic acid, unreacted formaldehyde, water and by-products. The unreacted propionic acid and unreacted formaldehyde are removed from the aqueous effluent and can be recycled.

BACKGROUND OF THE INVENTION

Unsaturated acids, such as methacrylic and acrylic acids, acrylonitrile, and the esters of such acids, such as methyl methacrylate, are widely used for the production of corresponding polymers, resins and the like. Various processes and catalysts have been proposed for the conversion of alkanoic acids, such as acetic acid or propionic acid, and formaldehyde to the corresponding unsaturated monocarboxylic acids, e.g., methacrylic acid, by an aldol-type reaction. Generally, the reaction of acid and formaldehyde takes place in the vapor or gas phase while in the presence of a basic or acidic catalyst.

The literature is replete with disclosures of the reaction of aliphatic carboxylic acid compounds with formaldehyde to produce alpha,beta-ethylenically unsaturated aliphatic monocarboxylic acid compounds of one more carbon atom than in the saturated carboxylic acid. For every molecule of alpha,beta-ethylenically unsaturated aliphatic monocarboxylic acid produced there is one molecule of water by-product. It is necessary to separate the alpha,beta-ethylenically unsaturated carboxylic acid compound, formaldehyde and the starting unsaturated carboxylic acid.

In the case of methacrylic acid, this means that the methacrylic acid must be separated from propionic acid, formaldehyde and water. This separation presents several problems since each of the components are water soluble and because propionic acid and methacrylic acid have boiling points that are so close that it is difficult to fractionate one from the other. Further, the separation is complicated by the fact that methacrylic acid has a tendency to homopolymerize and formaldehyde, if water is removed from the system, also has a tendency to homopolymerize. Of the various alpha,beta-ethylenically unsaturated compounds, it is generally recognized that methacrylic acid has one of the greatest tendencies to polymerize and it is extremely difficult to handle at elevated temperatures. In this regard, we have found that the presence of certain reaction by-products greatly increase the propensity of methacrylic acid to homopolymerize. Specifically, alpha-,beta-unsaturated ketones, i.e., ethylisopropenyl ketone and 2,5-dimethylcyclopenten-1-one, have been shown to greatly increase the degree of methacrylic acid homopolymerization. Additionally, methacrylic acid, propionic acid and formaldehyde individually form binary azeotropes with water. The boiling points of the three binary azeotropes are within 1° F. of each other and are thus exceedingly difficult to separate. The following table lists boiling points and weight percentages of binary azeotropes of water and methacrylic acid, propionic acid and formaldehyde at 760 mm Hg.

|  | Wt % | Wt % H$_2$O | B.P. °F. |
|---|---|---|---|
| Methacrylic acid | 23.1 | 76.9 | 210.7 |
| Propionic acid | 17.8 | 82.2 | 210.4 |
| Formaldehyde | 18.25–21.0 | 79.0–81.75 | 210.4 |

In somewhat greater detail, the invention relates to a process for an aldol-type condensation of a saturated aliphatic monocarboxylic acid compound and an aldehyde wherein said monocarboxylic acid is propionic acid and said aldehyde is formaldehyde. As is well-known, an aldol-type condensation can be base-catalyzed and is subject to ready dehydration if the $\beta$-hydroxyl group is adjacent to an $\alpha$-hydrogen atom. The product is an $\alpha,\beta$-unsaturated acid of one more carbon atom than the original unsaturated aliphatic monocarboxylic acid, when the reacting aldehyde is formaldehyde. The reaction using propionic acid and formaldehyde is:

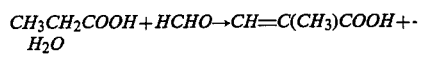

In the prior art a number of methods have been taught to overcome the aforementioned problems. A method for recovery of methacrylic acid from an aqueous effluent obtained by vapor phase condensation of formaldehyde and propionic acid, where the effluent contains unreacted formaldehyde and unreacted propionic acid, is taught in U.S. Pat. No. 4,040,913, wherein the recovery steps include extracting the effluent with an organic solvent capable of azeotroping with propionic acid to obtain an organic phase and an aqueous raffinate; distilling the organic phase to remove 50–100% of the unreacted propionic acid and leaving as bottoms remaining propionic acid and methacrylic acid; distilling the bottoms to obtain methacrylic acid as bottoms; and distilling the aqueous raffinate with an entrainer to obtain dilute aqueous formaldehyde overhead which is further concentrated by distillation. The aqueous raffinate and organic phase are separated by decantation.

Use of selective solvents for recovering unsaturated acids such as acrylic acid and methacrylic acid from aqueous mixtures is taught in the prior art. For example, U.S. Pat. No. 3,414,485 teaches a method of removing water from methacrylic acid in a two-stage process. In the first stage, methacrylic acid is extracted with an organic solvent which forms a minimum-boiling azeotrope with water. Suitable organic solvents include o-, m- and p-xylene, toluene, n-octane, monochlorobenzene, methylamylketone, ligroin and methyl methacrylate monomer. U.S. Pat. No. 3,478,093 teaches use of a lactam having 4 to 7 ring members and a hydrocarbon radical substituent on the nitrogen atom as an extraction solvent to separate methacrylic acid from aqueous mixtures. U.S. Pat. No. 3,781,332 teaches use of a dual mixture containing methyl or ethyl methacrylate and not more than 50% of xylene, ethyl benzene or a mixture thereof. U.S. Pat. No. 4,142,058 teaches use of a mixed solution of methyl methacrylate and toluene to separate methacrylic acid from an aqueous solution containing acetic acid. U.S. Pat. No. 4,147,721 teaches use of methyl n-propyl ketone.

Initially, it was believed by workers in this laboratory that it would be possible to separate methacrylic acid from propionic acid, formaldehyde and water by extraction and fractional distillation using a suitable solvent, such as an aliphatic hydrocarbon of from about 6 to 12 carbon atoms, as is taught in U.S. Pat. No. 4,409,128 or G.B. Pat. No. 2,001,315B. Unfortunately, attempts to implement the separation led to solid paraformaldehyde formation in the column between the feed location and the top of the column resulting in plugging of the column. The separation of these products is, of course, complicated by the fact that the unreacted saturated aliphatic carboxylic acid and formaldehyde must be recovered and returned to the main reactor in order to have an economically attractive process. Accordingly, the formation of solid paraformaldehyde in the column must be manageable from both an operational point of view and an economic point of view. Likewise, it is desirable to minimize the amount of unreacted formaldehyde that must be processed before returning same to the reactor.

The general object of this invention is to provide an improved method of treating the reaction product stream comprising the alpha,beta-ethylenically unsaturated aliphatic monocarboxylic acid compound of one more carbon atom than the starting saturated monocarboxylic acid compound, the saturated monocarboxylic acid compound, water, formaldehyde and by-products. A more specific object of this invention is an improved method of separating methacrylic acid, propionic acid, water, formaldehyde and by-products.

The objects of this invention can be attained by distilling the reaction product of a saturated aliphatic monocarboxylic acid compound and a formaldehyde compound comprising an alpha,beta-ethylenically unsaturated aliphatic monocarboxylic acid compound of one more carbon atom than the starting saturated aliphatic monocarboxylic acid compound, water and by-products, which comprises fractionally distilling said reaction products whereby a sidestream is removed from a location above the location of the feed stream input to the distillation column. In those cases where a distillation column is not in direct contact with a vessel or a reactor containing catalyst and is downstream from the reactor, the location of the sidedraw is located such that at least 10 (wt)% up to 95 (wt)% of the unreacted formaldehyde, and at least 10 (wt)% up to 70 (wt)% of the unreacted propionic acid in the column is removed from the column in the sidestream. The sidestream is composed of no more than 50 (wt)% water plus methacrylic acid. In a preferred method, the reaction products are distilled together with a substantially non-reactive compound capable of acting as a water-entrainer and of breaking a water azeotrope of said saturated aliphatic carboxylic acid compound under conditions whereby (1) a major proportion of the ethylenically unsaturated monocarboxylic acid compound remains in the bottom of the column, (2) a major portion of the water, a portion of the formaldehyde compound and a major portion of the compound capable of acting as a water-entrainer and of breaking or preventing the formation of said azeotrope are removed overhead and (3) a sidestream is removed below the top of the distillation column comprising water, a major portion of formaldehyde and a substantial proportion of saturated aliphatic carboxylic acid.

In the case of the separation of the reaction products of methacrylic acid, propionic acid, formaldehyde and water, we have found that by removing a sidestream below the top of the distillation column, it is possible to recycle a substantial portion of the unreacted formaldehyde and propionic acid to the reactor and avoid the polymerization and plugging of the distillation column by polymerized formaldehyde.

In addition, a major advantage of using a side draw stream and directly recycling this stream to the methacrylic acid synthesis reactor is the reduced costs in the overall process which accrue because unreacted propionic acid and formaldehyde do not have to be separated and individually purified.

In a preferred method of operation, the unreacted propionic acid and formaldehyde are recycled to the inlet ports of the reactor and employed to produce methacrylic acid.

SUMMARY OF THE INVENTION

A method is disclosed of distilling the reaction products of a saturated aliphatic monocarboxylic acid compound and formaldehyde compound, said reaction products comprising saturated aliphatic monocarboxylic acid compound, alpha,beta-ethylenically unsaturated aliphatic monocarboxylic acid compound of one more carbon atom than the starting saturated aliphatic monocarboxylic acid compound, water, formaldehyde and by-product which comprises fractionally distilling said reaction product whereby a sidestream is removed below the top of the distillation column comprising water, a major portion of unreacted formaldehyde and a substantial proportion of unreacted saturated aliphatic monocarboxylic acid.

DESCRIPTION AND PREFERRED EMBODIMENTS OF THE INVENTION

The process of this invention will be understood from the following description and examples.

The process of this invention is a process for the separation of alpha-,beta-ethylenically unsaturated monocarboxylic compounds of one more carbon atom than the starting saturated aliphatic monocarboxylic acid compound from the effluent stream. Particularly it is a process for the separation of methacrylic acid from the reactor effluent comprising methacrylic acid, propionic acid, formaldehyde, water and by-products.

The success of this method of separation of methacrylic acid from the reactor effluent stream is due primarily to the use of particular process conditions and process equipment, specifically a distillation tower with a side-draw means of separating a sidestream rich in formaldehyde and propionic acid. This sidestream contains 60–95 (wt)% of the unreacted formaldehyde and 10–70 (wt)% of the unreacted propionic acid entering the distillation column. This sidestream also contains a sufficient amount of water to prevent polymerization of formaldehyde and/or methacrylic acid with attendant plugging of the side-draw means. Water content of the side-draw stream can be within the range of from about 0.5 (wt)% to about 50 (wt)% of the side-draw stream. Water content will depend upon ratio of reactants in reactor feed, reaction temperature, and other process conditions.

The sidestream is suitable for direct recycle to the methacrylic acid synthesis reactor. The recycle of large percentages of unreacted formaldehyde and unreacted propionic acid directly back to the synthesis reactor reduces need for separation and purification of formaldehyde and propionic acid downstream and downsizes recovery equipment. Immediate recovery and immediate recycle of unreacted formaldehyde and unreacted propionic acid back to the synthesis reactor is an economic advantage. Reaction products of methacrylic acid and water are removed as bottoms and overhead respectively.

Location of the side-draw on the effluent distillation column is at a central part of the column and can be within a wide range over the column's height, from a low which is about 10% of the column theoretical trays to a high of about 90% of the column theoretical trays, preferably 30-85% of the column theoretical trays. Actual location of the side-draw can be determined by experiment, as location of the side-draw will be determined by reaction conditions, including composition of the reactor feed and effluent as well as conditions of the distillation unit operation, such as optional use of an entrainer.

A large number of catalysts, both water-tolerant and water-intolerant types, exhibit activity in the aldol-type condensation reaction of this invention. Specific catalyst materials that are useful in the process include synthetic alkali metal aluminosilicates, natural alkali metal aluminosilicates, synthetic alkaline earth metal aluminosilicates, natural alkaline earth metal aluminosilicates, alkali metal hydroxides on synthetic aluminosilicates, alkali metal hydroxides on natural aluminosilicates, alkaline earth metal hydroxides on synthetic aluminosilicates, alkali metal hydroxides on silica gel, alkaline earth metal hydroxides on silica gel, sodium silicate on silica gel, potassium silicate on silica gel, molybdenum oxide on silica gel, silica gel, synthetic manganese aluminosilicate, natural manganese aluminosilicate, synthetic cobalt aluminosilicate, natural cobalt aluminosilicate, synthetic zinc aluminosilicate, and natural zinc aluminosilicate.

Catalyst compositions found to be especially useful in the reaction to form methacrylic acid from propionic acid and formaldehyde are the subject of applications numbered Ser. No. 624,040 and Ser. No. 624,041 filed on even date in the names of Hagen, et al., and Kaduk, et al., respectively, which are hereby incorporated by reference.

The synthesis reactor feed stock can be composed of propionic acid, formaldehyde, and some water. The mole ratio of propionic acid to formaldehyde is preferably maintained within the range from about 25/1 to about 1/25; with a more preferred range of about 2/1 to ½. The feed stock or feed mixture can be obtained by adding the required amounts of propionic acid and formaldehyde to the recycle mixture of propionic acid and formaldehyde, to maintain the desired proportions.

The reaction takes place over a wide temperature range; temperatures in the range of about 280° C. to about 500° C. are satisfactory. Desirable and advantageous results are obtained by operating with temperatures in the range of about 280° C. to about 350° C. The process is normally run at atmospheric pressure, although higher or lower pressures can be used.

The space velocity of the vaporized feed mixture over the catalyst can be varied over wide limits. Space velocity figures in this specification are based on the total number of moles of materials entering the catalyst zone. Total moles are multiplied by the volume of a mole of an ideal gas at 0° C. and one atmosphere (22.4 liters/mole), to obtain the total volume under standard conditions. A space velocity in the range from about 100 liters per hour of the feed per liter of reactor volume to about 1000 liters per hour of the feed per liter of reactor volume is preferred.

Any of the various formaldehyde containing materials can be used with the catalyst of the process, such as formalin, methanolic formaldehyde solution, paraformaldehyde, and trioxane. Preferably, the formaldehyde compound is from about 99 (wt)% to about 70 (wt)% formaldehyde.

The reactor effluent stream contains water of reaction, one mole of water for each mole of methacrylic acid produced. Distillation with use of a side-draw separates unreacted propionic acid and unreacted formaldehyde with some percentage of water, from the reactor effluent. Methacrylic acid and remaining water are removed as bottoms and overhead, respectively. Alternatively, to separate the water from the propionic acid and methacrylic acid, a substantially non-reactive compound capable of acting as a water-entrainer and of breaking or preventing the formation of a water azeotrope of propionic acid can be introduced into the reactor effluent to break the water-propionic acid azeotrope upon distillation. The non-reactive compound alternatively can also be introduced into the reactor.

Because the product stream contains amounts of unreacted propionic acid and unreacted formaldehyde, as well as water, selection of a suitable hydrocarbon in a preferred method of operation wherein reactor effluent is distilled to separate the components is determined by the boiling points of azeotropes of propionic acid and methacrylic acid. Both propionic acid and methacrylic acid form water azeotropes which boil at approximately 99° C. Separation by distillation of the $C_6$ to $C_{12}$ hydrocarbon in the presence of water requires that the water:hydrocarbon azeotrope which forms having a boiling point below the boiling points of the propionic acid and methacrylic acid:water azeotropes. Preferably, the boiling point of the water:hydrocarbon azeotrope be no more than 95° C.

Boiling points of hydrocarbon:water azeotropes are:

| Hydrocarbon | % Water | B.P. °C. |
|---|---|---|
| n-Hexane | 5 | — |
| n-Heptane | 13 | 79 |
| n-Octane | 23 | 90 |
| n-Nonane | 40 | 95 |

Branched $C_6$ to $C_{12}$ saturated aliphatic hydrocarbons, aromatic hydrocarbons of 6 to 12 carbon atoms, cycloalkanes of 6 to 12 carbon atoms and mixtures thereof which form water:hydrocarbon azeotropes with boiling points of no more than 95° C. can be also used.

We have found that introduction of a suitable hydrocarbon non-reactive compound into the reactor can result in an increase in yield, based on propionic acid, of about 3% without any loss of reactants due to formation of additional by-products.

Suitable hydrocarbon compounds found to be useful in increasing the yield of methacrylic acid from propionic acid and formaldehyde are the subject of Ser. No. 624,050 filed an even date in the names of Hagen, et al, which is hereby incorporated by reference.

The hydrocarbon compound can be any hydrocarbon capable of azeotroping with water and not forming a multicomponent azeotrope with acid, as one of the components. Suitable entrainers include aliphatic saturated hydrocarbons of 6 to 12 carbon atoms such as hexane, heptane and octane, including isomers, as well as benzene, o-, m-, or p-xylenes, toluene and mixtures thereof. n-Heptane is preferred.

An essential process element of the process of the instant invention is distillation of the reactor effluent stream under process conditions utilizing a side-draw whereby, 60–90 (wt)% of the unreacted formaldehyde and 10–70 (wt)% of unreacted propionic acid entering the distillation column are removed for recycle to the synthesis reactor. If an entrainer is used, the distillation column overhead consists of water, the entrainer, a small amount of formaldehyde and a trace of propionic acid. The distillation column bottoms contain methacrylic acid, propionic acid and the heavy by-products of the methacrylic acid synthesis reaction. These bottoms are further processed to recover the methacrylic acid and the propionic acid. The overhead is sent to a formaldehyde recovery and dehydration section to remove the water. There, aqueous formaldehyde is reacted with an alcohol selected from the group consisting of 2-ethylhexanol, cyclohexanol and other commercially available heavy alcohols. A hemiacetal is formed with an alcohol, such as 2-ethyl-1-hexanol (2-EH) to form 2-ethylhexyl hemiformal, which is then dried. The dry hemiformal is subsequently thermally cracked, liberating dry formaldehyde for the reaction section. The waste water is sent to waste treatment.

In a specific embodiment, the synthesis reaction section in the instant process produces methacrylic acid and water via the base-catalyzed aldol-type condensation of propionic acid and formaldehyde. Conversions of propionic acid in the reactor range from 15 to 40%. Catalyst performance, irrespective of whether the catalyst is relatively water-tolerant or relatively water-intolerant, can be adversely affected over a long time period by the presence of significant quantities of water in the reactor feed. It has been learned that long-term water concentrations of greater than 2-4 (wt)% in the reactor feed can have a deleterious effect on long-time catalyst performance. High selectivities have been obtained from propionic acid and formaldehyde with typical catalysts, 80–95% and 75–90%, respectively. Major liquid reaction by-products have been identified as ethyl isopropenyl ketone, 3-pentanone, 2,5-dimethylcyclopen-ten-1-one, 2,2,4-trimethylbutyrolactone, and isobutyric acid. Carbon dioxide is also a by-product. Reactor effluent is necessarily processed to recover unreacted propionic acid, unreacted formaldehyde and methacrylic acid.

In a preferred embodiment, introduction of an entrainer into the reactor or into the reactor effluent in the effluent distillation tower serves to break the binary azeotropes which form. n-Heptane, as an example of an entrainer, is introduced into the reactor or into the reactor effluent to break the propionic acid-water azeotrope (BP 210° F.) with a lower boiling n-heptane-water azeotrope (BP 174.6° F.). With no n-heptane present, propionic acid would be carried overhead from the effluent distillation column in substantial amounts. The propionic acid-water azeotrope is 17.8 (wt)% propionic acid.

In a example of the method of operation, the effluent distillation tower consisted of a 40-tray two-inch vacuum jacket Oldershaw column equipped with a forced convection reboiler and a downflow condenser. Thermowells and sample taps were provided on every fifth tray of which several sample taps functioned as feed or product removal taps.

Surprisingly, it was found that at temperatures of from approximately 160° F. to 315° F. (at one atmosphere) over the length of the distillation column, high concentrations of unreacted propionic acid and unreacted formaldehyde occurred within the column at certain tray levels, permitting removal of the unreacted propionic acid and unreacted formaldehyde from the distillation column. The sidestream so removed from the distillation column can contain as much as 60–95 (wt)% of the unreacted formaldehyde and 10–70 (wt)% of the unreacted propionic acid contained in the synthesis reactor effluent. The sidestream can contain from about 0.5 (wt)% to about 10 (wt)% water and as much as 2–4 (wt)% methacrylic acid.

The resultant concentration ratio of water to formaldehyde in the sidestream is dependent upon synthesis reactor operating conditions, in particular, the propionic acid/formaldehyde mole feed ratio to the reactor, the formaldehyde conversion, the resulting water make in the reactor and the water concentration in the reactor feed. Surprisingly, it has been found that if an entrainer is used, control of the water content of the sidestream can be obtained by control of the ratio of entrainer to water in the feed to the column.

Since a completely anhydrous sidestream containing formaldehyde results in solids formation in the sidedraw, the sidestream water content is preferably at least 0.5 (wt)%. The formaldehyde species withdrawn in the sidestream are polyoxymethylene glycols whose average molecular weights increase with increasing formaldehyde/water mole ratios. The formation of solids (paraformaldehyde) in the sidedraw is aggravated by use of high vacuum which reduces operating temperatures. Accordingly, limits of temperature and pressure in the effluent distillation column are dependent upon the formaldehyde/water mole ratios in the column and side-draw temperature, formation of solids occurring in the side-draw at about 175° F. and a formaldehyde:water mole ratio of 15:1 or more.

In a specific embodiment, concentration of unreacted formaldehyde and unreacted propionic acid within the effluent distillation column is dependent upon temperature, pressure and sidedraw formaldehyde/water weight ratios. Polymerization of methacrylic acid in the effluent distillation column is conveniently prevented by addition of a suitable inhibitor which can be selected from the group consisting of p-benzoquinone, t-butylcatechol, and phenothiazine, as well as other well-known inhibitors (including oxygen) for the prevention of methacrylic acid polymerization. The following table gives operating conditions of the effluent distillation column:

| | |
|---|---|
| Number of Trays | 40 |
| Column Temperatures | |
| Overhead °F. | 160°–175° |
| Sidedraw °F. | 210°–250° |
| Bottoms °F. | 285°–315° |
| Column Pressure, Atm. | 1 |

-continued

| Sidedraw Formaldehyde/ | 20.3/2.09 |
| Water (Weight % Ratios) | to |
| | 41.2/3.5 |

Water content in the feed to the effluent distillation column is composed of water produced in the reactor and water content of the reactor feed. The following table gives suitable operating conditions of the methacrylic acid synthesis reactor.

| Water Concentration In Feed (wt) % | 1%–2% |
| Propionic Acid/Formaldehyde Mole Ratio | 3:2 to 1:1 |
| Methacrylic Acid Yield (Based on Propionic Acid) | 28–33 (wt) % |
| Water Concentration In Reactor Effluent (wt) % | 4%–8% |

In summary, the instant invention relates to a process for distilling the reaction product stream from a reactor of propionic acid, and a formaldehyde compound, the reaction product stream comprising propionic acid, formaldehyde, methacrylic acid and by-products which comprises fractionally distilling said reaction product stream whereby a sidestream is removed from the central part comprising from 10% to 90% of the theoretical trays of said distillation column. The location of the sidedraw is such that at least 10 (wt)% of the unreacted formaldehyde and at least 10 (wt)% of the unreacted propionic acid is removed from the column in the sidestream. The sidestream comprises not more than a total of 50 (wt)% water plus methacrylic acid.

The invention also comprises a method of distilling the reaction product stream of a saturated aliphatic monocarboxylic acid compound and a formaldehyde compound, said reaction product stream comprising said saturated aliphatic monocarboxylic acid compound, an alpha,beta-ethylenically unsaturated aliphatic monocarboxylic acid compound of one more carbon atom, water, said formaldehyde compound and by-products which comprises fractionally distilling said reaction product together with a substantially non-reactive compound capable of acting as a water-entrainer and of breaking or preventing the formation of a water azeotrope of said saturated aliphatic monocarboxylic acid compound under conditions whereby (1) a major proportion of ethylenically unsaturated monocarboxylic acid compound is in the bottom of the distillation column, (2) a major portion of the water, a portion of the formaldehyde compound and a major portion of the compound capable of breaking or preventing the formation of said azeotrope are removed overhead and (3) a sidestream is removed below the top of the distillation column comprising water, a major portion of said formaldehyde compound and a substantial portion of said saturated aliphatic monocarboxylic acid. The sidestream can be recycled back to the reactor.

Specifically, the invention comprises a method of treating the reaction products of propionic acid and formaldehyde which comprise methacrylic acid and water wherein the reaction products are fractionally distilled and unreacted propionic acid and unreacted formaldehyde are removed in a side-draw stream from the distillation column. Alternatively, the reaction products are distilled with an entrainer wherein the greater portion of water present is removed overhead, the substantial portion of unreacted propionic acid and major portion of unreacted formaldehyde are removed in a sidedraw stream and methacrylic acid and propionic acid are removed as bottoms.

Embodiments of the process of the present invention can be found in the following examples. These embodiments and examples are presented for purposes of illustration only and are not intended to limit the scope of the invention.

EXAMPLE I

Into a 2 inch vacuum jacketed Oldershaw distillation column containing 30 trays and 22 inches of 0.16 inch Pro Pack 316 stainless steel packing at the top, equivalent to about 10 to 20 theoretical trays, 1212.9 g/hr was fed at Tray No. 8 of simulated methacrylic acid (MA) reactor effluent having the following composition of formaldehyde (FA), water ($H_2O$), propionic acid (PA) and n-heptane ($C_7$),

| | FA | $H_2O$ | PA | MA | $C_7$ |
|---|---|---|---|---|---|
| (wt) %'s | 9.11 | 3.69 | 40.37 | 16.05 | 30.51 |

Also incorporated into the feed to prevent MA polymerization in the tower bottoms was 1000 ppm p-benzoquinone and 500 ppm phenothiazine. In addition 4500–5000 ppm oxygen (as 50 vol.% with nitrogen) was sparged into the reboiler of the column. All levels are based on MA in the feed.

As a control, actual pilot-plant reactor effluent containing small amounts of the by-products was fed to the reactor effluent column under nearly identical condition. Additional inhibitor was required to keep the system MA polymer free. The pilot plant reactor effluent had the composition of by-products described below;

| | (wt) % |
|---|---|
| 3-Pentanone | 0.034 |
| Isobutyric Acid | 0.05 |
| 2,5-Dimethylcyclopenten-1-one | 0.013 |
| 2,2,4-Trimethylbutyrolactone | 0.003 |

An inhibitor package of 1100 ppm p-benzoquinone, 1100 ppm t-butylcatechol and 550 ppm phenothiazine together with an oxygen addition rate of 10,000 ppm oxygen (all based on MA fed to the column) allowed operation with no visible evidence of MA polymers.

The column was operated at atmospheric pressure with the temperature at various locations in the column as follows:

| Column Bottoms | Feed Tray No. 8 | Sidedraw Tray No. 18 | Column Overhead |
|---|---|---|---|
| 296° F. | 264° F. | 220° F. | 169° F. |

The compositions and takeoff rates for the column bottoms, sidedraw (Tray No. 18) and overhead are given below.

| | Rate | Composition Analysis (wt) % | | | | |
|---|---|---|---|---|---|---|
| Location | (g/HR) | FA | $H_2O$ | PA | MA | $C_7$ |
| Overhead | | | | | | |
| Aqueous | 59.9 | 25.69 | 72.60 | 1.71 | — | ~0 |

-continued

| Location | Rate (g/HR) | Composition Analysis (wt) % | | | | |
|---|---|---|---|---|---|---|
| | | FA | H$_2$O | PA | MA | C$_7$ |
| Organic | 373.8 | — | — | — | — | ~100 |
| Sidedraw | 238.3 | 41.22 | 3.50 | 52.12 | 2.36 | 0.8 |
| Bottoms | 553.6 | <0.01 | 0.07 | 65.23 | 34.69 | ~0 |
| | 1225.6 g | (101.0% Theory) | | | | |

The (wt)% of FA (unreacted FA) and PA (unreacted PA) in the sidestraw stream correspond to 88.9% of the FA fed to the column and 25.4% the PA fed to the column.

EXAMPLE II

When the column and condition as described in Example I were used to distill a feed as described in Example I without removing a sidedraw stream the formation of solid paraformaldehyde in the column between Tray No. 20–30 caused column plugging and the resultant failure of the system to operate.

EXAMPLE III

In the procedure of Example I, the same composition of formaldehyde and propionic acid was fed to the distillation column. Excess water, in the amount to make the H$_2$O/FA ratio in the column 3/1 or greater, was added. The dilution of the formaldehyde was below the level at which solids formation occurred. However, it was determined that separation of the water component in the tower overhead would entail a heavy energy penalty.

EXAMPLE IV

In the procedure of Example I, the same composition of formaldehyde, propionic acid and water was fed to the distillation column. Excess heptane, in the amount to azeotrope all the water in the feed, was added above the feed point of the column so that only heptane was used as the reflux to the column. All the water and excess formaldehyde was removed overhead. The overhead with the high formaldehyde content condensed as paraformaldehyde in the condenser, plugging the condenser tubes. In addition propionic acid loss in this overhead stream was excessive.

What is claimed is:

1. A process of distilling a reaction product formed by the reaction between a saturated aliphatic monocarboxylic acid compound and a formaldehyde compound and comprising unreacted saturated aliphatic monocarboxylic acid compound, an alpha,beta-ethylenically unsaturated aliphatic monocarboxylic acid compound of one more carbon atom than the starting saturated aliphatic monocarboxylic acid compound, water, unreacted formaldehyde compound and by-products, which comprises fractionally distilling said reaction product whereby a sidestream comprising unreacted saturated aliphatic monocarboxylic acid compound and unreacted formaldehyde compound is removed from the central part of a distillation column, said alpha,beta-ethylenically unsaturated aliphatic monocarboxylic acid and water being removed as bottoms and overhead respectively.

2. The process of claim 1 wherein the total (wt)% water plus said alpha-beta-ethylenically unsaturated aliphatic monocarboxylic acid compound in said sidestream is not more than 50 (wt)%.

3. The process of claim 1 wherein said saturated aliphatic monocarboxylic acid compound is propionic acid and said alpha-,beta-ethylenically unsaturated aliphatic monocarboxylic acid compound is methacrylic acid.

4. The process of claim 1 wherein said formaldehyde compound is selected from the group consisting of formalin, methanolic formaldehyde solution, paraformaldehyde and trioxane.

5. The process of claim 1 wherein said formaldehyde compound is from about 99 (wt)% to about 70 (wt)% formaldehyde.

6. The process of claim 1 wherein said reaction product is distilled in said column at conditions of:

| Column Temperatures | |
|---|---|
| Overhead °F. | 160°–175° |
| Sidedraw °F. | 210°–250° |
| Bottoms °F. | 285°–315° |
| Column Pressure, Atm. | 1 |

7. The process of claim 1 wherein said sidestream comprises from 10 (wt)% up to 95 (wt)% of unreacted formaldehyde compound and from 10 (wt)% up to 70 (wt)% of unreacted saturated monocarboxylic acid compound in said reaction product.

8. A process of distilling a reaction product formed by the reaction between a saturated aliphatic monocarboxylic acid compound and a formaldehyde compound and comprising unreacted saturated aliphatic monocarboxylic acid compound, an alpha,beta-ethylenically unsaturated aliphatic monocarboxylic acid compound of one more carbon atom than the starting saturated aliphatic monocarboxylic acid compound, water, unreacted formaldehyde compound and by-products, which comprises fractionally distilling said reaction product together with a non-reactive compound which entrains water and breaks or prevents the formation of a water azeotrope of said saturated aliphatic monocarboxylic acid compound under conditions whereby (1) a major proportion of said ethylenically unsaturated monocarboxylic acid compound is in the bottom of a distillation column, (2) a major portion of the water, a portion of aid formaldehyde compound and a major portion of said compound capable of breaking or preventing the formation of said azeotrope are removed overhead and (3) a sidestream comprising unreacted saturated aliphatic monocarboxylic acid compound and unreacted formaldehyde compound is removed from the central part of said distillation column.

9. The process of claim 8 wherein said non-reaction compound is a hydrocarbon of from 6 to 12 carbon atoms.

10. The process of claim 8 wherein said non-reactive compound is selected from the group consisting of n-hexane, n-heptane, n-octane and their isomers, benzene, o-, m-, or p-xylene, toluene and mixtures thereof.

11. The process of claim 8 wherein said non-reactive compound is n-heptane.

12. The process of claim 8 wherein said non-reactive compound is introduced into the reactor producing said reaction product.

13. The process of claim 8 wherein said nonreactive compound forms a water-non-reactive compound azeotrope.

14. The process of claim 1 wherein said sidestream is recycled to said reactor.

* * * * *